(12) United States Patent
Chen et al.

(10) Patent No.: US 7,531,185 B2
(45) Date of Patent: May 12, 2009

(54) MASK COMPOSITION CONTAINING EMULSIFIED LIQUID COMPOSITION

(75) Inventors: Minghua Chen, Hyogo (JP); Miwa Miyamoto, Hyogo (JP); Yin-Jang Chen, Hyogo (JP); David Leigh Trigg, Hyogo (JP); Zi-Hua Fu, Hyogo (JP)

(73) Assignee: The Procter & Gamble Company, Cincinnati, OH (US)

( * ) Notice: Subject to any disclaimer, the term of this patent is extended or adjusted under 35 U.S.C. 154(b) by 791 days.

(21) Appl. No.: 10/622,518

(22) Filed: Jul. 18, 2003

(65) Prior Publication Data

US 2004/0018166 A1    Jan. 29, 2004

Related U.S. Application Data

(60) Provisional application No. 60/397,374, filed on Jul. 19, 2002.

(51) Int. Cl.
*A01N 25/34* (2006.01)

(52) U.S. Cl. ...................... 424/402; 424/400

(58) Field of Classification Search ............... None
See application file for complete search history.

(56) References Cited

U.S. PATENT DOCUMENTS

| | | | |
|---|---|---|---|
| 5,716,599 A | | 2/1998 | Golz et al. |
| 5,747,022 A * | | 5/1998 | Slavtcheff ............... 424/78.03 |
| 6,042,844 A | | 3/2000 | Ishida et al. |
| 6,083,854 A * | | 7/2000 | Bogdanski et al. .......... 442/157 |
| 6,753,063 B1 * | | 6/2004 | Pung et al. .................. 428/152 |
| 2002/0155772 A1* | | 10/2002 | Wong et al. ................. 442/123 |
| 2005/0238698 A1* | | 10/2005 | Simon et al. ................ 424/443 |

FOREIGN PATENT DOCUMENTS

| | | |
|---|---|---|
| EP | 0 063875 A2 | 11/1982 |
| EP | 0 950391 A1 | 10/1999 |
| FR | 2271808 A | 12/1975 |
| JP | 2000044427 A2 | 2/2000 |
| JP | 2000063230 A2 | 2/2000 |
| JP | 2002114664 | 4/2002 |
| JP | 20020249423 | 9/2002 |
| JP | 20030342125 | 12/2003 |
| WO | WO00028961 | 5/2000 |

OTHER PUBLICATIONS

JP 242509 (Feb. 22, 1994) Abstract.*

* cited by examiner

*Primary Examiner*—Jyothsna A Venkat
(74) *Attorney, Agent, or Firm*—Eric T. Addington; Brian M. Bolam; Tara M. Rosnell (57) ABSTRACT

Disclosed is a mask composition comprising:
(1) a water insoluble substrate; and
(2) an emulsified liquid composition comprising:
  (a) an oily component;
  (b) a hydrophilic surfactant;
  (c) a water-soluble thickening polymer which provides the liquid composition a viscosity of from about 500 mPa·s to about 60,000 mPa·s; and
  (d) an aqueous carrier.

2 Claims, 2 Drawing Sheets

MASK COMPOSITION CONTAINING EMULSIFIED LIQUID COMPOSITION

CROSS REFERENCE TO RELATED APPLICATION

This application claims the benefit of U.S. Provisional Application No. 60/397,374, filed on Jul. 19, 2002.

FIELD OF INVENTION

The present invention relates to a mask composition for topical application, wherein the mask comprises a water insoluble substrate and an emulsified liquid composition.

BACKGROUND OF THE INVENTION

Masks designed for providing treatment to the skin are known in the art, such as SKII Facial Treatment Mask on the Japanese market. Such masks are made of a substrate and a liquid soaked in the substrate, wherein the mask is adhered only very weakly to the skin, such that the mask is easily removed from the skin with practically no tension to the skin. These treatment masks can be distinguished from removal masks. Removal masks are those designed to firmly adhere to the skin and thereby remove dirt, clogs, and excess corneum on the surface and in the pores of skin upon peeling off the mask. Treatment masks are particularly suitable for applying to the skin for delivering moisturizing agents and other benefit agents to the skin through a wet, typically aqueous, environment. In fact, delivery of moisturizing agents and other benefit agents via a mask is advantageous in that the skin is exposed to an abundant amount of such agents over a lengthy period of time. Treatment masks also provide relaxation benefit to the user upon use, because the usage encourages the user to sit or lay down. Treatment masks are generally applied to the facial skin.

Although these treatment masks provide some skin conditioning benefits such as moisturized feel by the use of moisturizing agents, consumers who are conscious of their skin desire treatment masks which provide improved skin conditioning benefits such as smoothness and softness, in addition to moisturized feel.

Based on the foregoing, there is still a need for a mask composition which provides improved skin conditioning benefits, and particularly, a mask composition which provides smoothness, softness, and moisturized feel to the skin.

None of the existing art provides all of the advantages and benefits of the present invention.

SUMMARY OF THE INVENTION

The present invention is directed to a mask composition comprising:
(1) a water insoluble substrate; and
(2) an emulsified liquid composition comprising:
  (a) an oily component;
  (b) a hydrophilic surfactant;
  (c) a water-soluble thickening polymer which provides the liquid composition a viscosity of from about 500 mPa·s to about 60,000 mPa·s; and
  (d) an aqueous carrier.

These mask compositions can provide improved conditioning benefits such as smoothness, softness, and moisturized feel to the skin upon use.

These and other features, aspects, and advantages of the present invention will become better understood from a reading of the following description, and appended claims.

All documents cited are, in relevant part, incorporated herein by reference; the citation of any document is not to be construed as an admission that it is prior art with respect to the present invention.

BRIEF DESCRIPTION OF THE DRAWINGS

While the specification concludes with claims particularly pointing out and distinctly claiming the invention, it is believed that the present invention will be better understood from the following description of preferred, nonlimiting embodiments and representations taken in conjunction with the accompanying drawings in which:

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "topical application" means to apply or spread a material onto the surface of the skin.

Herein, "cosmetically-acceptable" means that the compositions or components thereof so described are suitable for use in contact with human skin without undue toxicity, incompatibility, instability, allergic response, and the like.

Herein, "mixtures" is meant to include a simple combination of materials and any compounds that may result from their combination.

All ingredients such as actives and other ingredients useful herein may be categorized or described by their cosmetic and/or therapeutic benefit or their postulated mode of action. However, it is to be understood that the active and other ingredients useful herein can, in some instances, provide more than one cosmetic and/or therapeutic benefit or operate via more than one mode of action. Therefore, classifications herein are made for the sake of convenience and are not intended to limit an ingredient to the particularly stated application or applications listed.

Water-Insoluble Substrate

The mask compositions of the present invention comprise a water-insoluble substrate. By "water insoluble", it is meant that the substrate does not dissolve in or readily break apart upon immersion in water. The water-insoluble substrate is the implement or vehicle for delivering the liquid composition to the skin.

A wide variety of materials can be used as the substrate. The following nonlimiting characteristics are desirable: (i) sufficient wet strength for use, (ii) sufficient abrasivity, (iii) sufficient thickness, (iv) appropriate size, (v) air permeability, and (vi) hydrophobicity.

Nonlimiting examples of suitable substrates which meet the above criteria include nonwoven substrates, woven substrates, hydroentangled substrates, air entangled substrates, natural sponges, synthetic sponges, polymeric netted meshes, and the like. Preferred embodiments employ nonwoven substrates since they are economical and readily available in a variety of materials. By "nonwoven", it is meant that the layer is comprised of fibers which are not woven into a fabric but rather are formed into a sheet, mat, or pad layer.

The substrates may be comprised of a variety of materials both natural and synthetic. Nonlimiting examples of natural materials useful in the present invention include: silk fibers; keratin fibers such as wool fibers and camel hair fibers; and cellulose fibers such as wood pulp fibers, cotton fibers, hemp fibers, jute fibers, and flax fibers. Nonlimiting examples of synthetic materials useful in the present invention include: acetate fibers; acrylic fibers; cellulose ester fibers; polyamide fibers; polyester fibers such as polyethylene terephthalate fibers; polyolefin fibers such as polypropylene fibers and polyethylene fibers; polyvinyl alcohol fibers; rayon fibers; and polyurethane foam.

Substrates useful in the present invention can also be obtained from a wide variety of commercial sources. Nonlimiting examples of suitable nonwoven substrates useful herein include: WALKISOFT®, a cellulose substrate available from Walkisoft U.S.A.; NOVONET® 149-801 and 149-191, a substrate containing about 69% rayon, about 25% polypropylene, and about 6% cotton, available from Veratec, Inc. Walpole, Mass.; KEYBAK® 951V and 1368, a substrate containing about 75% rayon and about 25% acrylic fibers, available from PGI/Chicopee, Dayton, N.J.; RMT-90, a 3-layer substrate having a pulp layer as an inner layer with outer layers respectively made of the combination of rayon and polyester, and RFP-90, a 3-layer substrate having a combined PP layer as an inner layer with outer layers of rayon, both available from Daiwabo K.K.

The substrate can be made into a wide variety of shapes and forms such as flat pads, thick pads, thin sheets, and sheets of irregular thickness, depending on the desired use and characteristic of the mask. The substrate is typically designed to fit the area of the skin to which topical application is desired. For example, when the mask is applied to the face, the substrate is designed to correspond to the shape of the face avoiding the eye, nostril, and mouth areas, as necessary.

Figure 1:
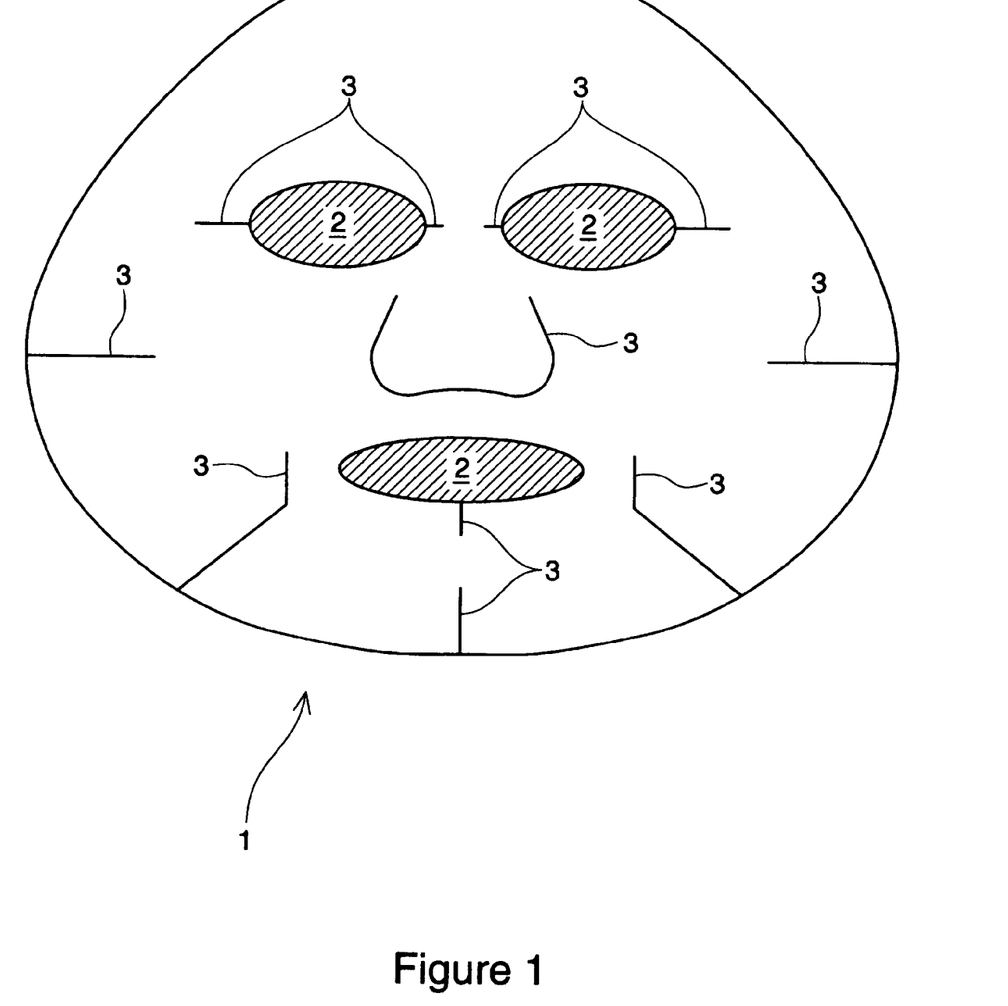
FIG. 1 is a plane view of a preferred embodiment of the water-insoluble substrate of the present invention.

In one preferred embodiment, the substrate is so configured to cover substantially the whole area of the facial skin with areas of the eyes and nostrils opened. Referring to FIG. 1, a plane view of a particularly preferred embodiment of a substrate suitable for a single-piece whole facial mask (10) is depicted. The outer peripheral of the substrate of FIG. 1 is designed to approximately match the contour of the face, with a plurality of openings (12) for the eyes and the mouth, and wherein a plurality of cuttings (13) are made so that the mask fits the nose, cheeks, and the mouth. The embodiment of FIG. 1 has a length of from about 15 cm to about 25 cm, preferably from about 18 cm to about 23 cm, and a width of from about 15 cm to about 30 cm, preferably from about 20 cm to about 25 cm; to cover the average entire facial area. In another preferred embodiment, the substrate is so configured to cover substantially the whole area of the facial skin, and is made of two pieces, the first piece covering the upper area of the face, i.e. the nose and thereabove, and the second piece covering the lower area of the face, i.e. the upper lip, cheeks and thereunder. In another preferred embodiment, the substrate is so configured to match the area of a particular part of the face, such as the nose, cheekbone, chin, forehead, or combinations thereof. In another preferred embodiment, the substrate is so configured to have ears, pulls, or rings for facilitating placement and/or removal of the mask on the skin.

The substrate is flexible enough such that, when soaked with the liquid composition, readily fits along the skin, yet strong enough so that it does not easily tear or crumble upon use. Preferably, the substrate has a thickness of from about 100 μm to about 1 cm, more preferably from about 300 μm to about 3 mm, depending on the material for making the substrate, and use and characteristic of the product.

Substrate materials particularly useful herein include those which are of hydrophilic nature, thereby capable of absorbing a larger quantity of the liquid composition. The water-insoluble substrate can be made solely of hydrophilic material, or made of a mixture of hydrophilic material and hydrophobic material. The substrates of the present invention can consist of a single layer or multiple layers. In one preferred embodiment, the substrate is made of at least partially by hydrophilic materials selected from cotton, pulp, rayon, and mixtures thereof. By partially, it is meant to encompass following situations: where one layer of a hydrophilic material is used for a single layered substrate; where at least one layer of a hydrophilic material is used for a multiple layered substrate; where one layer of a mixture of the hydrophilic material and another material is used for a single layered substrate; and where at least one layer of a mixture of the hydrophilic material and another material is used for a multiple layered substrate.

When the substrate consists of multiple layers, it is preferred that at least the layer facing the skin is that of hydrophilic nature, thereby capable of absorbing a larger quantity of the liquid composition. When the substrate consists of multiple layers, the substrates can include films and other nonfibrous materials. In one embodiment, the substrate may also be laminated with polymeric film on the substrate, coating the substrate, or heat sealing the substrate. The resulting substrate with the laminated polymeric film, coating or heat sealing comprises an occluded side on one side of the substrate, which faces away from the skin, and a skin facing side that is positioned on the skin surface. By having a substrate with an occluded side, the substrate acquires low air permeability. By "low air permeability" it is meant that the side of the substrate having the film, coating or heat sealing allows very little air to enter into the substrate and very little vapor to escape from the substrate. Preferably the air permeability is less than about 5 mg/cm$^2$/min, more preferably between about 0.01 mg/cm$^2$/min and about 4.8 mg/cm$^2$/min. The air permeability can be measured by taking the weight of a fully saturated sample of the substrate and weighing the substrate after it is exposed to the atmosphere.

Figure 2:
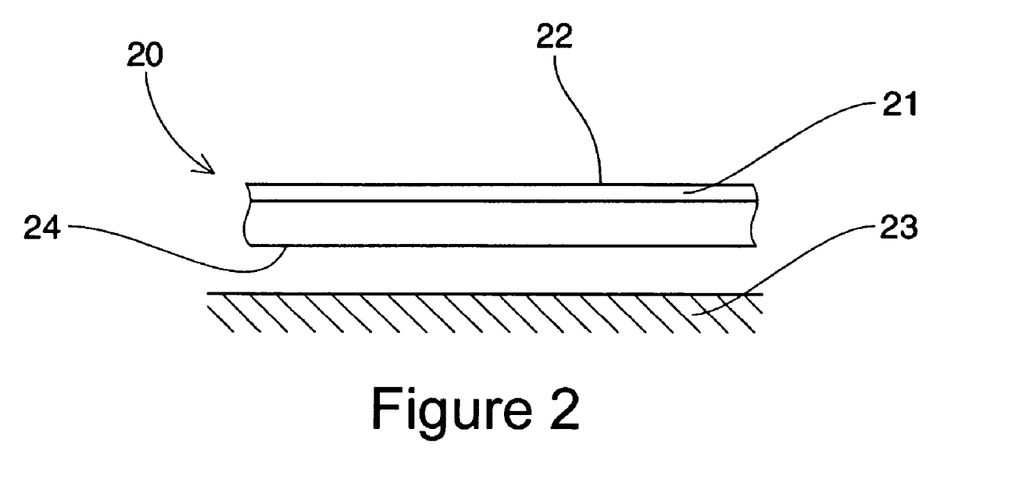
FIG. 2 is an inflated cross sectional view of the water-insoluble substrate having an occluded side.

An embodiment of a substrate having an occluded side having low air permeability is shown in FIG. 2. As shown in FIG. 2, a substrate (20) is laminated with a polymer film (21), forming an occluded side (22). The polymer film (21) is greatly exaggerated to show detail. The occluded side (22), is placed away from the skin surface (23) during use. The occluded side (22) restricts moisture from escaping into the atmosphere during a typical use time period between about 5 minutes to about 45 minutes thus providing improved moisturizing effect to the skin. The skin facing side (24) of the substrate (20) preferably does not contain any materials that restrict air permeability.

A substrate comprising an occluded side significantly increases penetration of oily components and skin benefit agents into the skin compared to a substrate without an occluded side. Without being limited by a theory, it is believed that the occluded side (22) of the substrate (20) allows for the creation of a humid environment near the surface of the skin by limiting the evaporation of water from the mask composition into the atmosphere. Additionally, the mask composition of the present invention utilizes water tension to adhere to the skin surface rather than strong adhesives on the skin facing side. The absence of a strong adhesive between the substrate and the skin surface, as utilized by the present invention, removes the physical barrier resulting from the strong adhesive and promotes the penetration of the oily components and other skin benefit agents. The resulting environment between the skin and the substrate promotes the penetration of the oily components and other skin benefit agents into the skin.

Suitable polymeric film includes polyethylene, polypropylene, polyethylene terephtalate, polyamides, polyesters, nylons, blends thereof, or any other cosmetically acceptable polymeric films. Suitable coatings include any materials know in the art that impart low air permeability to the substrate and are cosmetically acceptable. Heat-sealing the substrate may be accomplished by any method known in the art to impart low air permeability to the substrate.

In one embodiment, the substrate comprises a layer having a gradients of hydrophilic properties, i.e., having a gradient of distribution of hydrophobic materials and hydrophilic materials. In this substrate, it is preferred that the substrate has a high distribution of hydrophilic materials at the skin facing side, and a high distribution of hydrophobic materials at the opposite side. This structure allows for moisture to be move from the hydrophobic side of the substrate to the hydrophilic skin facing side of the substrate to the skin surface. This substrate can be a single layered substrate, can further comprise other layers, or can be laminated with a polymeric film.

Emulsified Liquid Composition

The mask compositions of the present invention comprise an emulsified liquid composition in addition to the water-insoluble substrate described hereinbefore. The mask composition of the present invention comprises an emulsified liquid composition that impregnates, coats or is otherwise in contact with the water-insoluble substrate described hereinbefore.

The emulsified liquid composition herein comprises:
(a) an oily component;
(b) a hydrophilic surfactant wherein the surfactant is preferably nonionic;
(c) a water-soluble thickening polymer which provides the liquid composition a viscosity of from about 500 mPa·s to about 60,000 mPa·s; and
(d) an aqueous carrier.

The amount of liquid composition associated with any individual mask composition will vary depending upon the desired characteristics of the finished mask composition product, but should be at least an amount sufficient to result in deposition of the oily components and other skin benefit agents onto the skin during application to provide benefits thereof. The mask compositions of the present invention are preferably saturated with the liquid composition such that the water-insoluble substrate remains saturated with the liquid composition. To that desired end, the liquid composition will therefore preferably represent from about 100% to about 2000%, more preferably from about 200% to about 1500%, by weight of the water-insoluble substrate. By the phrase "remains saturated with the liquid composition," as used herein means that the substrate is not dried during the interval between the saturation of the mask composition with the liquid composition and application of the mask composition to the skin. The amount of liquid composition to be used will depend on the absorbing capability of the water-insoluble substrate, and the desired characteristic of the mask composition.

The liquid compositions used for the mask composition of the present invention have a viscosity in the range of from about 500 mPa·s to about 60,000 mPa·s, preferably from about 1000 mPa·s to about 30,000 mPa·s, more preferably from about 200 mPa·s to about 15,000 mPa·s, as measured by a Brookfield Digital Viscometer, Model DV-II+ Version 3.2 according to the operating instructions set forth in Manual No. M/92-161-H895, with speed 5.0 rpm. Such viscosity is believed to be suitable for penetrating into the water insoluble substrate while providing reduced dripping down from the face during application. Such viscosity is also believed to be suitable for suspending particulate materials, when included, in the liquid composition in an effective manner, as well as effectively depositing the particulate materials to the skin.

Oily Component

The emulsified liquid composition of the present invention comprises oily components. Oily components useful herein can deliver skin conditioning benefits such as smoothness and softness to the skin. Oily components useful herein include, for example, fatty alcohols, silicone oils, mineral oil, petrolatum, $C_{7-40}$ straight and branched hydrocarbons such as isohexadecane, $C_{1-30}$ alcohol esters such as isopropyl isostearate, glycerides, alkylene glycol esters, propoxylated and ethoxylated derivatives, sugar ester such as sucrose polycottonseedate, vegetable oils such as coconut oil, hydrogenated vegetable oils, animal fats and oils, and $C_{4-20}$ alkyl ethers of polypropylene glycols, $C_{1-20}$ carboxylic acid esters of polypropylene glycols, and di-$C_{8-30}$ alkyl ethers. Hydrophobic nonionic surfactants, which are those being water-insoluble and having an HLB value of less than 10, can be used as oily components. Hydrophobic nonionic surfactants useful herein include, for example, cetearyl glucoside, steareth-2, laureth-4, sucrose cocate, sorbitan monoisostearate, sorbitan diisostearate, sorbitan sesquiisostearate, sorbitan monooleate, sorbitan dioleate, sorbitan sesquioleate, glyceryl monoisostearate, glyceryl diisostearate, glyceryl sesquiisostearate, glyceryl monooleate, glyceryl dioleate, glyceryl sesquioleate, diglyceryl diisostearate, diglyceryl dioleate, diglycerin monoisostearyl ether, diglycerin diisostearyl ether, and mixtures thereof.

Among the above oily components, highly preferred are fatty alcohols, in that they provide skin conditioning benefits, and also in that they can form gel networks with surfactants which provide increased viscosity, phase stability, and conditioning benefits such as slippery feel. The fatty alcohols useful herein are a saturated, linear or branched fatty alcohol, selected from the group consisting of a saturated, linear or branched $C_{12-30}$ fatty alcohols, a saturated, linear or branched $C_{12-30}$ diols, and mixtures thereof. Preferred fatty alcohols are cetyl alcohol, stearyl alcohol, and mixtures thereof.

The oily components are included in the liquid composition at a level by weight of, preferably from about 0.01% to about 10%, more preferably from about 0.05% to about 5%, still more preferably from about 0.1% to about 3%, in view of providing skin conditioning benefits such as smoothness while providing reduced stickiness and slippery feel.

Hydrophilic Surfactant

The liquid composition of the present invention comprises hydrophilic surfactants. The hydrophilic surfactants are included in the composition at a level by weight of, preferably from about 0.01% to about 10%, more preferably from about 0.05% to about 5%, still more preferably from about 0.1% to about 2%.

Hydrophilic surfactants useful herein are those being water-soluble, and preferably have an HLB value of above 10. Hydrophilic surfactants useful herein include, for example, any cosmetically acceptable surfactants, i.e., nonionic surfactants, cationic surfactants, anionic surfactants, zwitterionic surfactants, amphoteric surfactants, and mixtures thereof. Among them, preferred herein are cosmetically acceptable nonionic surfactants in view of reduced skin irritation and conditioning benefits.

Hydrophilic nonionic surfactants useful herein include, for example, PEG-100 stearate, polysorbate-20, polysorbate-60, seteareth-21, isoceteth-20, and oleth-20, laureth-23, ceteareth-12, steareth-100, PEG 40 hydrogenated castor oil, PEG-60 hydrogenated castor oil, and mixtures thereof.

Water Soluble Thickening Polymer

The liquid compositions of the present invention comprise a water-soluble thickening polymer. The water soluble thickening polymers herein are water soluble or water miscible polymers, have the ability to increase the viscosity of the composition, and are compatible with other components used in the composition. The water-soluble thickening polymer is selected so that the liquid composition of the present composition has the desired viscosity of from about 500 mPa·s to about 60,000 mPa·s, preferably from about 1000 mPa·s to about 30,000 mPa·s, more preferably from about 2000 mPa·s to about 15,000 mPa·s. The water soluble thickening polymers are included, by weight of the liquid composition, at a level preferably from about 0.1% to about 3%, more preferably from about 0.1% to about 2%, still preferably from about 0.2% to about 2%.

Water soluble thickening polymers useful herein include anionic polymers and nonionic polymers. The water soluble thickening polymers useful herein include, for example, acrylic polymers, polyalkylene glycol polymers having a molecular weight of more than about 10000, celluloses and derivatives there of such as hydroxyethyl cellulose, polyvinylpyrrolidone, polyvinyl alcohol, gums such as guar gum and xanthan gum, carragenan, pectin, agar, quince seed (Cydonia oblonga Mill), starch (rice, corn, potato, wheat), algae colloids (algae extract), dextran, succinoglucan, pulleran, carboxymethyl starch, methylhydroxypropyl starch, sodium alginate, and alginic acid propylene glycol esters. Neutralizing agents may be included to neutralize the anionic thickening agents described hereinabove. Nonlimiting examples of such neutralizing agents include sodium hydroxide, potssium hydroxide, ammonium hydroxide, monethanolamine, diethanolamine, triethanolamine, diisopropanolamine, aminomethylpropanol, tromethamine, tetrahydroxypropyl ethylenediamine, and mixtures thereof.

Among the above polymers, highly preferred are those providing reduced undesirable polymer flakes when emulsified liquid compositions are dried on the skin. Such highly preferred polymers include, for example, acrylic polymers. Acrylic polymers useful herein include those comprising monomers selected from the group consisting of acrylic acid, salts of acrylic acid, derivatives of acrylic acid, methacrylic acid, salts of methacrylic acid, derivatives of methacrylic acid, and mixtures thereof. The derivatives include, for example, alkyl acrylate, acrylamide, alkyl metahcrylate, and methacrylamide. Such acrylic polymers include, for example, cross linked acrylic acid polymers with the CTFA name Carbomer, sodium polyacrylate, polyethylacrylate, polyacrylamide, and acrylic acid/alkyl acrylate copolymers with the CTFA name Acrylates/C10-30 Alkyl Acrylate Crosspolymer. Commercially available acrylic polymers highly useful herein include, for example, polyacrylamide with tradename Sepigel 305 available SEPPIC Inc., and Acrylates/C10-30 Alkyl Acrylate Crosspolymer having tradenames Pemulen TR-1, Pemulen TR-2, Carbopol 1342, Carbopol 1382, and Carbopol ETD 2020, all available from B. F. Goodrich Company.

Aqueous Carrier

The liquid compositions of the present invention comprise an aqueous carrier. The level and species of the carrier are selected according to the compatibility with other components, and other desired characteristic of the product. The aqueous carrier is contained in the composition at a level by weight of, preferably from about 30% to about 99%, more preferably from about 50% to about 95%, still more preferably from about 70% to about 95%.

Carriers useful in the present invention include water and water solutions of lower alkyl alcohols. Lower alkyl alcohols useful herein are monohydric alcohols having 1 to 6 carbons, more preferably ethanol. Preferably, the aqueous carrier is substantially water. Deionized water is preferably used. Water from natural sources including mineral cations can also be used, depending on the desired characteristic of the product.

The pH of the present composition is preferably from about 4 to about 8. When skin benefit agents are included in the liquid composition, the pH may be adjusted to that which provides optimum efficacy of the active skin benefit agents. Buffers and other pH adjusting agents can be included to achieve the desirable pH. Suitable pH adjusters herein include acetates, phosphates, citrates, triethanolamines and carbonates.

Water Soluble Humectant

The liquid composition of the present invention preferably contain a water soluble humectant as a skin benefit agent. Water soluble humectants are preferably included to provide moisturizing benefit to the skin. Further, water soluble humectants may help the dispersion of the water soluble thickening agents, and dissolving/dispersion of other components which are relatively difficult to process in an aqueous carrier. The water soluble humectants may be included, by weight of the liquid composition, at a level preferably from about 0.1% to about 30%, more preferably from about 1% to about 20%, still preferably from about 5% to about 15%.

Water soluble humectants useful herein include polyhydric alcohols such as glycerin, diglycerin, propylene glycol, dipropylene glycol, butylene glycol, hexylene glycol, sorbitol, ethoxylated glucose, 1,2-hexane diol, hexanetriol, erythritol, trehalose, xylitol, maltitol, maltose, glucose, fructose, sodium chondroitin sulfate, sodium hyaluronate, sodium adenosin phosphate, sodium lactate, pyrrolidone carbonate, glucosamine, cyclodextrin, and mixtures thereof.

Water soluble humectants useful herein also include water soluble alkoxylated nonionic polymers such as polyethylene glycols and polypropylene glycols having a molecular weight of up to about 1000 such as those with CTFA names PEG-200, PEG-400, PEG-600, PEG-1000, and mixtures thereof.

Chronic Whitening Agent

The liquid composition may include a chronic whitening agent as a skin benefit agent. The chronic whitening agent useful herein refers to active ingredients that not only alter the appearance of the skin, but further improve hyperpigmentation as compared to pre-treatment. By definition, chronic is referred to continued topical application of the composition over an extended period during the subject's lifetime, preferably for a period of at least about one week, more preferably for a period of at least about one month, even more preferably for at least about three months, even more preferably for at least about one year. Typically, applications would be on the order of about once per day over such extended periods, while application rates can vary from about once per week up to about three times per day or more. The chronic whitening agents may be included, by weight of the liquid composition, at a level preferably from about 0.001% to about 10%, more preferably from about 0.1% to about 5%.

Useful chronic whitening agents useful herein include ascorbic acid compounds, vitamin $B_3$ compounds, azelaic acid, butyl hydroxy anisole, gallic acid and its derivatives, glycyrrhizinic acid, hydroquinoine, kojic acid, arbutin, mulberry extract, ergothioneine, and mixtures thereof. Among them, preferred are ascorbic acid compounds, vitamin $B_3$ compounds, and mixtures thereof. Use of combinations of chronic whitening agents are believed to be advantageous in that they may provide whitening benefit through different mechanisms.

Ascorbic acid compounds useful herein include, ascorbic acid per se in the L-form, ascorbic acid salt, and derivatives thereof. Ascorbic acid salts useful herein include, sodium, potassium, lithium, calcium, magnesium, barium, ammonium and protamine salts. Ascorbic acid derivatives useful herein includes, for example, esters of ascorbic acid, and ester salts of ascorbic acid. Particularly preferred ascorbic acid compounds include 2-o-α-D-glucopyranosyl-L-ascorbic acid, which is an ester of ascorbic acid and glucose and usually referred to as L-ascorbic acid 2-glucoside or ascorbyl glucoside, and its metal salts, and L-ascorbic acid phospate ester salts such as sodium ascorbyl phophate, potassium ascorbyl phosphate, magnesium ascorbyl phosphate, and calcium ascorbyl phosphate. Commercially available ascorbic compounds include 2-o-α-D-glucopyranosyl-L-ascorbic acid available from Hayashibara and sodium L-ascorbyl phosphate with tradename STAY C available from Roche.

Vitamin $B_3$ compounds useful herein include, for example, those having the formula:

wherein R is —$CONH_2$ (e.g., niacinamide) or —$CH_2OH$ (e.g., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide. Preferred vitamin $B_3$ compounds are niacinamide and tocopherol nicotinate, and more preferred is niacinamide. In a preferred embodiment, the vitamin $B_3$ compound contains a limited amount of the salt form and is more preferably substantially free of salts of a vitamin $B_3$ compound. Preferably the vitamin $B_3$ compound contains less than about 50% of such salt, and is more preferably essentially free of the salt form.

Skin Tone Changing Agent

The liquid compositions of the present invention may include a skin tone changing agent as a skin benefit agent. The skin tone changing agent useful herein are selected from the group consisting of skin tone changing pigments, reflective particulate material, and mixtures thereof. Skin tone changing agents useful herein are those altering the appearance of the color and/or tone of the skin including, but not limited to, skin whitening. The skin tone changing agents have a particle size of, preferably at least about 100 nm.

The skin tone changing pigments useful herein include, for example, talc, mica, silica, magnesium silicate, titanium oxide, zinc oxide, and titanium oxide coated mica.

The reflective particulate materials useful herein have a primary particle size of from about 100 nm to about 10 μm (i.e., in the essentially pure, powder form prior to combination with any carrier). The reflective particulate materials can be inorganic. The inorganic reflective particulate materials useful herein include, for example, titanium dioxide, zinc oxide, more preferably the particles consist essentially of titanium dioxide. The inorganic reflective particulate materials can be coated with a coating material such as cationic polymers, cationic surfactants, anionic polymers, and anionic surfactants.

Additional Components

Additional components may be included in the liquid compositions in view of the desired characteristics of the mask composition. Such additional components are included at a level that does not alter the function of the essential components of the mask composition of the present invention, typically no more than about 5% by weight of the liquid composition.

Additional Skin Benefit Agent

The composition of the present invention may include additional skin benefit agents including, but are not limited to, anti-acne agents, anti-oxidants and radical scavengers, anti-inflammatory agents, antimicrobial agents, and skin texture improvement agents.

Anti-acne agents useful herein include salicylic acid, 4-methoxysalicylic acid, benzoyl peroxide, lactic acid, metronidazole, panthenol, retinoic acid and its derivaties, sulphur, triclosan, and mixtures thereof.

Anti-oxidants and radical scavengers useful herein include, for example, tocopherol (vitamin E), esters of tocopherol such as tocopherol acetate and tocopherol nicotinate, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, amines (i.e., N,N-diethylhydroxylamine, amino-guanidine), sulfhydryl compounds (i.e., glutathione), dihydroxy fumaric acid and its salts, lycine pidolate, arginine pilolate, nordihydroguaiaretic acid, bioflavonoids, lysine, methionine, proline, superoxide dismutase, silymarin, tea extracts, grape skin/seed extracts, melanin, and rosemary extracts.

Anti-inflammatory agents useful herein include, for example, alpha bisabolol, aloe vera, Manjistha (extracted from plants in the genus Rubia, particularly *Rubia Cordifolia*), and Guggal (extracted from plants in the genus Commiphora, particularly *Commiphora Mukul*), kola extract, chamomile, and sea whip extract, and the licorice (the plant genus/species Glycyrrhiza glabra) family including glycyrrhetic acid, glycyrrhizic acid, and derivatives thereof (e.g., salts and esters).

Antimicrobial agents useful in the present invention include benzoyl peroxide, erythromycin, tetracycline, clindamycin, azelaic acid, sulfur resorcinol phenoxyethanol, and IRGASAN® DP 300 (Ciba Geigy Corp., U.S.A.).

Skin texture improvement agents useful herein include niacinamide, esters of nicotinic acid, nicotinyl alcohol, panthenol, panthenyl ethyl ether, n-acetyl cysteine, n-acetyl-L-serine, phosphodiesterase inhibitors, trimethyl glycine, tocopheryl nicotinate, and vitamin $B_3$ and analogues or derivatives, and mixtures thereof. Panthenol is particularly preferred. Panthenol is commercially available, for example, by Roche.

Skin vitalizing agents useful herein include seaweed extracts such as algae extract and *Laminaria Digitata* extract.

Other Components

In addition to the above described components, the composition of the present invention may further include preservatives and preservative enhancers such as water-soluble or dispersible preservatives including methyl paraben, propyl paraben, imidazolidinyl urea, Germall 115, methyl, ethyl, propyl and butyl esters of hydroxybenzoic acid, benzyl alcohol, EDTA, Bronopol (2-bromo-2-nitropropane-1,3-diol) and phenoxypropanol; ultraviolet light absorbers or scattering agents; sequestrants; anti-androgens; depilation agents; soluble or colloidally-soluble moisturizing agents such as hyaluronic acid and starch-grafted sodium polyacrylates such as SANWET® IM-1000, IM-1500 and IM-2500 available from Celanese Superabsorbent Materials, Portsmith, Va., USA and described in U.S. Pat. No. 4,076,663; proteins and polypeptides and derivatives thereof; organic hydroxy acids; drug astringents; external analgesics; film formers; anticaking agents; antifoaming agents; binders; coloring agents; perfumes, essential oils, and solubilizers thereof; natural extracts; guai-azulene; and yeast ferment filtrate.

Method of Preparation

The mask composition of the present invention can be made by any method known to the artisan. Generally, the mask composition is made by placing the water-insoluble substrate in a housing, pouring in the liquid composition so that the water-insoluble substrate soaks the liquid composition, and sealed for delivery and/or storage. The mask composition can be housed in a package per unit or by multiple units. By "unit" what is meant is, for example, a single piece facial mask would make a unit by itself, while a two-piece facial mask would make a unit by one upper piece mask and one lower piece mask. Preferably, the mask composition is housed in individual packaging per unit. For single use packaging, the packaging is hermetically sealed and opened upon use. For multiple use packaging, the packaging is equipped by a means so that the packaging can be substantially hermetically sealed after opening.

Method of Use

The mask composition of the present invention is suitable for topical application on human body skin, particularly facial skin. The use of the present composition provides skin conditioning benefits such as smoothness, softness, and moisturized feel to the skin due to the deposition and penetration of oily components. Other benefits to the skin can be provided by application of the present mask composition in view of the specific benefit agents such as chronic whitening agents and skin benefit agents included in the emulsified liquid composition. The mask composition of the present invention is particularly advantageous in delivering the oily components and other benefit agents in that the skin is exposed to an abundant amount of such agents over a lengthy period of time. Compared to when the liquid composition is applied to the skin without the use of the insoluble substrate, the use of the mask composition of the present invention, with the insoluble substrate as a delivery means over a lengthy period, is believed to provide better distribution and deposition of such agents, and better penetration of those agents which are percutaneously deliverable. Further, when an insoluble substrate having low air permeability is used, more effective penetration of the skin benefit agents into the skin is expected. The mask composition of the present invention is also believed to provide emotional benefits to the user upon use, such as refreshing feel, and relaxation feel.

In one preferred embodiment, the mask composition is used to treat the facial skin by the steps of:

(a) applying the mask composition to the majority of the area of the facial skin;

(b) allowing the mask composition to stand on the facial skin for a period of time no longer than until any portion of the mask composition is dried;

(c) removing the mask composition from the facial skin; and (d) removing the remainder liquid composition left on the facial skin.

The mask composition is soaked with an aqueous liquid composition, thus the mask fits to the facial skin by gently placing on the skin. For better fit and even distribution of the oily components and other skin benefit agents, the mask is pressed to the facial skin using finger tips.

By definition, "dried" refers to a state wherein water and other volatile components such as perfume, if included, evaporates from the water insoluble substrate, thereby leaving the substrate significantly less capable of delivering the oily components and other benefit agents to the skin. Thus, once a portion of the mask is dried, even distribution of the oily components cannot be expected. Further, when dried, the mask composition provides an unpleasant stiff and tough feeling to the skin when applied.

Because the mask composition of the present invention is easily dried via exposure to regular atmospheric conditions, the mask composition must be housed in a hermetically sealed package during storage.

The period of time required until dried portions appear will depend on the atmosphere in which the use takes place, i.e. temperature, humidity, air circulation; and the structure and body temperature of the user. Typically, the mask composition should be designed so that no dried portions appear within a period of about 15 minutes when used in room temperature at a humidity of about 50%. When an insoluble substrate having low air permeability is used, the period of time by which the mask composition is dried can be prolonged, preferably from about 5 to about 45 minutes.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

The mask compositions of Example 1 through 6 are made of about 3.0 g of substrate RFP-90 available from Daiwabo, cut and shaped according to FIG. 1 and soaked with 25 g each of the emulsified liquid compositions specified below. The mask compositions can also be made of 3.5 g of cotton substrate instead of the substrate specified above.

Emulsified Liquid Composition

| Components | Ex. 1 | Ex. 2 | Ex. 3 | Ex. 4 | Ex. 5 | Ex. 6 |
|---|---|---|---|---|---|---|
| Isopropyl isostearate | 0.5 | 0.5 | 0.5 | 0.5 | 0.5 | 0.5 |
| Sucrose polycottonseedate | 0.25 | — | 0.25 | — | 0.25 | — |
| Cetyl alcohol | 0.2 | 0.3 | 0.2 | 0.3 | 0.3 | 0.2 |
| Stearyl alcohol | 0.2 | 0.3 | 0.2 | 0.3 | 0.3 | 0.2 |
| Isohexadecane | — | 0.2 | — | — | — | — |
| Mineral oil | — | — | — | — | 2.0 | — |
| Coconut oil | — | 0.2 | — | — | 0.2 | — |
| PEG-100 stearate | 0.1 | 0.1 | 0.1 | 0.1 | 0.1 | 0.1 |
| Polysorbate 20 *1 | — | — | 0.3 | — | 0.3 | — |
| Steareth-21 | — | 0.2 | 0.1 | — | 0.5 | — |
| Cetearyl glucoside | 0.1 | — | 0.1 | 0.15 | 0.1 | 0.1 |
| Steareth -2 | — | 0.2 | — | — | 0.1 | — |
| Polyacrylamide *2 | 1.2 | — | 1.2 | — | 1.5 | — |
| Acrylates/C10-30 Alkyl Acrylate Crosspolymer *3 | — | 0.25 | — | 0.25 | — | — |
| Xanthan gum *4 | — | — | — | — | — | 0.5 |
| Glycerin | 3.0 | — | 3.0 | 3.0 | 3.0 | 3.0 |
| 1,3-butylene glycol | 5.0 | 5.0 | 5.0 | 5.0 | 5.0 | 5.0 |
| Dipropylene glycol | — | 3.0 | — | — | 4.0 | 4.0 |
| Titanium dioxide *5 | — | — | 0.1 | — | — | 0.1 |
| Ascorbyl glucoside *6 | — | 2.0 | — | — | — | 2.0 |
| Sodium Ascorbyl phosphate *7 | — | — | — | — | 0.5 | — |
| Niacinamide *8 | 3.5 | 2.0 | 2.0 | — | — | 1.0 |
| Panthenol *9 | — | — | 1.0 | — | — | — |
| Tocopherol Acetate *10 | — | 0.2 | — | — | — | — |
| Tocopherol Nicotinate *11 | 0.5 | — | — | 0.5 | 0.5 | 0.5 |
| Sodium salicylate | — | 0.2 | — | 0.5 | — | 0.5 |
| Mulberry extract *12 | 0.5 | — | 0.5 | — | 0.5 | 0.5 |
| Yeast Ferment Filtrate *13 | — | — | — | — | — | 30 |
| Natural extracts *14 | 0.05 | — | — | — | — | 0.01 |
| Ergothioneine *15 | — | — | 0.02 | — | — | 0.01 |
| Laminaria Digitata extract *16 | — | — | 0.1 | — | — | 0.01 |
| Perfume | 0.05 | — | — | — | 0.1 | 0.03 |
| Benzyl alcohol | 0.15 | 0.15 | 0.15 | 0.15 | 0.15 | 0.15 |
| Ethyl paraben | 0.07 | 0.07 | 0.07 | 0.07 | 0.07 | 0.07 |
| Propyl paraben | 0.03 | 0.03 | 0.03 | 0.03 | 0.03 | 0.03 |
| Disodium EDTA | 0.1 | 0.1 | 0.05 | 0.1 | 0.1 | 0.1 |
| NaOH | Adjust pH to 6-8 | | | | | |
| Deionized Water | q.s. to 100% | | | | | |

Definitions of Components
*1 Polysorbate 20: Tween 20 available from ICI Surfactants
*2 Polyacrylamide: Sepigel 305 available from SEPPIC Inc.
*3 Acrylates/C10-30 Alkyl Acrylates Crosspolymer: Pemulen TR-2 available from B. F. Goodrich
*4 Xanthan gum: Keltrol available from Kelco
*5 Titanium dioxide: Kobo GLW75CAP-MP available from Kobo Products Inc.
*6 Ascorbyl glucoside: Available from Hayashibara.
*7 Sodium Ascorbyl phosphate: Stay-C available from Roche
*8 Niacinamide: Niacinamide available from Roche
*9 Panthenol: DL-Panthenol available from Roche
*10 Tocopherol acetate: Available from Eisai Co. Ltd.
*11 Tocopherol nicotinate: Available from Eisai Co. Ltd.
*12 Mulberry extract: mulberry extract BG available from Maruzen Pharmaceuticals
*13 Yeast Ferment Filtrate: SKII Pitera available from Kashiwayama
*14 Natural extracts: Phytelene EGX 243 [A mixture of Arnica Mountan Flower Extract, Hypericum Perforatum Extract, Ivy (*Hedera Helix*) extract, witchhazel (*Hamamelis Virginiana*) extract, grape (*vitis vinifera*) Leaf extract, and horse chestnut (*aesculus hippostanum*) extract] available from Kaneda.
*15 Ergothioneine: Thiotaine available from AGI Dermatics
*16 *Laminaria Digitata* extract: Seanergilium BG available from Coletica Method of Preparation The compositions above described can be made by any method known to the artisan. The compositions are suitably made as follows:

(1) Any oily component and hydrophilic surfactants are mixed in a vessel, and heated to 70° C. or above in order to melt solid oily compounds if included.
(2) Water-soluble and heat-stable ingredients other than water soluble thickening polymers are dissolved in water in another vessel, and heated to 70° C. or above.
(3) The products of steps (1) and (2) are mixed until homogeneous.
(4) Water soluble thickening polymers are added to the product of step (3) and mixed until homogeneous.
(5) The product of step (4) is cooled down to 40° C. or below.
(6) If included, other remaining components such as perfumes and yeast ferment filtrate are added to the product of step (5).
(7) The water-insoluble substrate is folded and placed in an aluminum pouch per one unit.
(8) The emulsified liquid composition thus obtained at step (6) is poured into the aluminum pouch containing the water-insoluble substrate, and hermetically sealed.

The embodiments of the present invention disclosed and represented above have many advantages. When applied to the face using finger tips for good fit and left for about 15 minutes, they provide improved skin conditioning benefits such as smoothness, softness, and moisturized feel to the skin.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A method of conditioning the facial skin comprising the steps of:
    (a) applying a mask composition to the majority of the area of the facial skin; wherein the mask comprises:
        (1) a water insoluble three-layer substrate, wherein said substrate comprises an inner layer and two outer layers, wherein said inner layer is polypropylene and said outer layers is rayon fibers, wherein the substrate comprises eye openings and a mouth opening; and
        (2) an emulsified liquid composition comprising:
            (i) from about 0.01% to about 10% of an oily component;
            (ii) from about 0.1% to about 10% of a hydrophilic nonionic surfactant;
            (iii) from about 0.1% to about 30% of a water-soluble thickening polymer which provides the liquid composition a viscosity of from about 500mPa•s to about 60,000mPa•s, wherein said water-soluble thickening polymer contains an acrylic polymer;
            (iv) from about 0.1% to about 30% of a water-soluble humectant;
            (v) from about 0.001% to about 10% of a chronic whitening agent, wherein said chronic whitening agent contains at least an ascorbic acid derivative and a vitamin $B_3$ derivative; and (iv) an aqueous carrier;

(b) allowing the mask composition to stand on the facial skin for a period of time no longer than until any portion of the mask composition is dried, wherein said period of time is from about 5 to about 45 minutes;

(c) removing the mask composition from the facial skin; and (d) removing the remainder liquid composition left on the facial skin.

2. The method of any of claim 1 wherein, at step (a), the mask is applied and fit on the facial skin by pressing on the mask to the facial skin using finger tips.

* * * * *